United States Patent [19]

Vick et al.

[11] Patent Number: 5,005,416

[45] Date of Patent: Apr. 9, 1991

[54] INSECT DETECTION USING A PITFALL PROBE TRAP HAVING VIBRATION DETECTION

[75] Inventors: Kenneth W. Vick, Newberry; J. C. Webb, Gainesville; Carl A. Litzkow, Newberry, all of Fla.

[73] Assignee: The United States of America as represented by the Secretary of Agriculture, Washington, D.C.

[21] Appl. No.: 525,016

[22] Filed: May 18, 1990

Related U.S. Application Data

[63] Continuation-in-part of Ser. No. 332,901, Apr. 4, 1989, Pat. No. 4,937,555.

[51] Int. Cl.$^5$ ............................................. G01N 29/00
[52] U.S. Cl. ......................................... 73/587; 43/121
[58] Field of Search ................... 73/587, 591; 367/139; 43/121

[56] References Cited

U.S. PATENT DOCUMENTS

| | | | |
|---|---|---|---|
| 3,336,573 | 8/1967 | Gallaway et al. | 340/7 |
| 3,494,329 | 2/1970 | Frieberger et al. | 73/584 X |
| 3,792,204 | 2/1974 | Murayama et al. | 179/110 A |
| 3,969,927 | 7/1976 | Yoshida et al. | 73/71.4 |
| 4,028,688 | 6/1977 | Goleman | 340/539 |
| 4,030,233 | 6/1977 | Wunsche | 43/121 |
| 4,309,576 | 1/1982 | Corrigan | 179/110 A |
| 4,415,979 | 11/1983 | Hernandez | 364/508 |
| 4,535,205 | 8/1985 | Ravinet et al. | 179/110 A |
| 4,583,405 | 4/1986 | Simmons | 73/584 |
| 4,671,114 | 6/1987 | Litzkow et al. | 73/587 |
| 4,809,554 | 3/1989 | Shade et al. | 73/587 |
| 4,895,025 | 1/1990 | Betts | 73/587 |
| 4,937,555 | 6/1990 | Litzkow et al. | 73/587 |
| 4,941,356 | 7/1990 | Pallaske | 73/587 |

FOREIGN PATENT DOCUMENTS

2517833 10/1983 France .

OTHER PUBLICATIONS

K. M. Reese, "ARS People Listen to Insects Inside Fruit", Chemical and Engineering News, Jul. 8, 1985, p. 56.
Pyrah, David, "New System Hears Insects Chewing", Agricultural Research, Apr., 1985, pp. 13–15.
Gourevitch, David; "Researchers 'listen' for Flies Inside Fruit", Gainesville Sun, Sunday Jun. 9, 1985.
New York Times, Jul. 1985, Science Watch "Listening to Larvae Chew".
The Atlanta Journal, Tuesday, Aug. 13, 1985, "Fruit Flies Chomp Away While Scientists Listen In".
The Phoenix Gazette, Wednesday, Jul. 24, 1985.
Discover Magazine, Aug. 1985, p. 10, "Maggots Unmasked".
Popular Science, Nov. 1985, Science Newsfront by Arthur Fisher, "Fruitful Listening".

*Primary Examiner*—Hezron E. Williams
*Assistant Examiner*—Rose M. Finley
*Attorney, Agent, or Firm*—David R. Sadowski; M. Howard Silverstein

[57] ABSTRACT

Detection, and optionally quantification, of insect infestation in an agricultural commodity is provided by a pitfall probe trap which permits detection of the presence or absence of live insects in the trap and optionally estimation of the number of insects in the trap. The present invention may be utilized to detect infestation by a variety of different insects such as: red flour beetle, lesser grain borer, rice weevil, rusty grain beetle, and saw tooth grain beetle; in numerous types of agricultural commodities including corn, wheat, rice, seeds, nuts, oats, barley, cotton or any similar commodity which may be infested during storage. Various embodiments are disclosed including use of the traps in a device for telemetry, in various container means for containing an agricultural commodity including e.g. truck, ship, railroad car or storage bin such as a silo or grain elevator.

29 Claims, 4 Drawing Sheets

West, Dick; "The Lighter Side", Tuesday, Jul. 2, 1985.
"Amplifier Spots Termites", Popular Mechanics, Nov., 1955, p. 97.
Webb, J. C. et al., "Detecting Insect Larvae in Fruit by Vibrations Produced", J. Environ. Sci. Health, A19(3), 367–375, (1984).
Hagstrum, D. W. et al., "Acoustical Detection and Estimation of Rhyzopertha Dominica (F.) Larval Populations In Stored Wheat", Florida Entomologist, vol. 71, No. 4, Dec. 1988.
Webb, J. C. et al., "A Computerized Acoustical Larval Detection System", Applied Eng. in Agr., vol 4 (3): 9/88, pp. 268–274.
Vick, K. W. et al., "Sound Detection of Stored-Product Insects that Feed Inside Kernels of Grain", J. Ec. Ent. 81:1489–1493, 1988.
Webb, J. C. et al., "Acoustical System to Detect Larvae in Infested Commodities"; Fla. Ent. 71(4), Dec. 1988, pp. 492–504.
BNF Enterprises Peabody Mass., Catalog No. 85P1, 1985, 4 pages.
Barax, A. V. and P. K. Harein; 1981, "Insect infestation of Farm-Stored Shelled Corn and Wheat in Minnesota", J. Econ. Entomol. 74(2):197–202.
Barak, A. V. and P. K. Harein; 1982, "Trap Detection of Stored Grain Insects in Farm-Stored, Shelled Corn"; J. Econ. Entomol. 75:108–111.
Burkholder, W. E. 1984; "Stored-product Insect Behavior and Pheromone Studies: Keys To Successful Monitoring And Trapping"; pp. 20–23; In Proc. 3rd Intl. Wkg. Conf. Stored Prod. Entomol., Kansas State University, Manhattan, Kans.
Fargo, W. S., D. Epperly, G. W. Cuperus, B. C. Clary, and R. Noyes, 1989. "Effects of Temperature and Duration of Trapping on Four Stored Grain Insect Species", J. Econ. Entomol. 82(3):970–973.
Hagstrum, D. W., G. Milliken, and M. S. Waddell; 1985, "Insect Distribution in Bulk-Stored Wheat in Relation to Detection or Estimation of Abundance", Environmental Entomol. 14(6):655–661.
Lippert, G. E. and D. W. Hagstrum; 1987, "Detection or Estimation of Insect Populations in Bulk-Stored Wheat with Probe Traps", J. Econ. Entomol. 80(3):601–604.
Loschiavo, S. R. 1975; "Field Tests of Devices to Detect Insects In Different Kinds of Grain Storage", The Canadian Entomol. 107:385–389.
Loschiavo, S. R. and J. M. Atkinson, 1967; "A trap for the Detection and Recovery of Insects in Stored Grain", Can. Entomol. 99:1160.
Loschiavo, S. R. and J. M. Atkinson; 1973, "An Improved Trap to Detect Beetles (Coleoptera) in Stored Grain", Can. Entomol. 105:437–440.
Subramanyam, Bh., P. K. Harein, and L. K. Cutkomp, 1989; "Field Tests with Probe Traps for Sampling Adult Insects Infesting Farm-Stored Grain", J. Agric. Entomol. 6(1):9–21.
White, N. D. G. and S. R. Loschiavo, 1986; "Effect of Insect Density, Trap Depth, and Attractants on the Capture of *Tribolium castaneum* and *Cryptolestes ferrugineus* in Stored Wheat", J. Econ. Ent. 79(4):1111–1117.

INSECT DETECTION USING A PITFALL PROBE TRAP HAVING VIBRATION DETECTION

CROSS-REFERENCE TO RELATED APPLICATION

The present application is a continuation-in-part of application Ser. No. 07/332,901 filed Apr. 4, 1989 now U.S. Pat. No. 4,937,555, issued June 26, 1990 entitled "Piezoelectric Apparatus and Process for Detection of Insect Infestation in an Agricultural Commodity" by Carl A. Litzkow, J. C. Webb and Kenneth W. Vick.

FIELD OF THE INVENTION

This invention relates to apparatus and processes for nondestructive, and inexpensive detection (and optionally quantification) of insect infestation in agricultural commodities.

BACKGROUND

In this country alone, hidden insect infestation in stored agricultural commodities such as corn, wheat, rice, seeds, oats, barley, cotton, etc., costs the government and farmers millions of dollars each year. This figure is obviously larger when considered on a worldwide basis. Quick, inexpensive, and reliable tools for determining insect infestation are needed, and could prove very beneficial in: (1) determining if a stored commodity is marketable; (2) maintaining good quality of agricultural commodities, and; (3) facilitating enforcement of government food quality regulations.

Various detection methods used in the past included X-ray, chemical or visual analysis, and more recently, acoustical amplification of insect sounds as exemplified by U.S. Pat. No. 4,671,114 issued June 9, 1987 to Litzkow et al. All of these methods are expensive, require elaborate testing facilities with trained personnel, and have various drawbacks. For example, X-ray inspection suffers from the drawbacks of: (1) high initial cost for equipment; (2) high cost of X-ray film and development, and; (3) examination of each of the individual grains on the X-ray film requires a great deal of labor. Acoustic detection such as that disclosed by the aforementioned U.S. Pat. No. 4,671,114 suffers from the drawbacks of: (1) requiring extensive acoustical detection elements which are not necessary for the present invention; (2) being susceptible to interference from extraneous sound thus requiring operation thereof in a sound dampened environment, in contrast to the present invention which provides similar sensitivity but surprisingly is not as susceptible to such interference.

Pitfall probe traps (some types of these are termed "Loschiavo" traps after S. R. Loschiavo who first described them in "A trap for the detection and recovery of insects in stored grain" Can. Entomol. 99:1160:1967) are commonly used in the grain industry to detect insect infestations. Insect infestation is commonly detected by burying such traps in grain, and capturing adult insects that wander into the perforated top part of the trap and fall into the reservoir located at the bottom of the trap. The trap is pulled from the grain mass by means of a rope and the number of insects captured is an indication of the level of the insect infestation in the grain. A shortcoming of this trap is that although traps can be positioned all the way to the bottom of a tall grain silo before it is filled with grain, once the trap is pulled up to check for insects, it is difficult or impossible to reinsert it in the grain to depths of more than a few feet. This invention allows the remote detection of the presence (and optionally the quantity) of insects without pulling the trap from the agricultural commodity. Thus, traps can remain in place even at considerable depths where they can continually monitor for insect infestations for an extended period of time (e.g. for a full storage season).

One embodiment described in the aforementioned parent application relates to a probe which was designed to detect insect infestations by insertion thereof in an agricultural commodity and counting the number of insect produced sounds detected by the probe. The number of insect produced sounds varies with the insect population density in the agricultural commodity and thus the population could be estimated by the number of detected sounds. There are many situations where this type of grain probe would be very useful, especially, where a quick decision was needed about whether grain was infested or not. However, the number of sounds detected by such a probe may depend both on the density of the insect infestation and on the distance between the insect and the probe. This latter parameter can make accurate estimation of the number of insects in a bin of agricultural commodity very difficult. Grain attenuates the insect produced sounds such that insects near the probe will produce many more detectable sounds than insects located farther from the probe. This attenuation can effect the estimated number of insects in the agricultural commodity by as much as 100 fold. For example, if the grain probe detected "X" number of sounds in a bin of grain, one may not know if these sounds were produced by one insect very close to the piezoelectric disc or possibly 100 insects located farther from the disc. Thus a marked improvement in insect estimation could be achieved, if this "distance" factor could be eliminated from the picture. The present invention does just that. By ensuring that all detected insects are confined in the proximity of the detection means (e.g. essentially confined on a surface of the detection means) the distance factor is removed from the infestation estimation problem.

SUMMARY

Accordingly several objects and advantages of our invention include:

avoiding the aforementioned draw backs and providing novel, advantageous and highly unobvious detection (and optionally quantification with greatly increased accuracy of insect density measurement) of insect infestation in an agricultural commodity;

to accomplish the foregoing in a quick, inexpensive, reliable and accurate manner;

to provide the aforementioned detection (and optionally quantification) for an extended period of time without the necessity for removing the insect pitfall probe trap from the agricultural commodity thereby saving substantial time and effort;

to provide continuous insect surveillance even in very large facilities;

to accomplish the foregoing in a manner which does not require trained personnel, elaborate testing facilities, or extensive acoustical detection elements;

to provide increased agricultural commodity quality by providing better insect surveillance and thereby facilitating timely and accurate use of insect control measures, and;

to provide for such detection (and optionally quantification) a device which is reliable, durable, compact, light weight and portable.

These and other objects of the instant invention which will become readily apparent from the ensuing description are accomplished utilizing an insect pitfall probe trap including:

an insect-permeable trap portion including a first wall portion defining therein a first interior chamber, said first wall portion defining at least one aperture dimensioned to permit ingress of an insect through said at least one aperture into said first interior chamber;

a reservoir portion including container means for containing at least one insect and defining a container means interior surface, said container means defining therein a second interior chamber dimensioned to contain therein at least one insect, said container means including on at least said interior surface thereof a non-stick material upon which insects cannot readily climb;

said insect permeable trap portion being connected to said reservoir portion whereby said first interior chamber is in insect-tight communication with said second interior chamber so that an insect may move from said first interior chamber to said second interior chamber;

means positioned between said first interior chamber and said second interior chamber for permitting movement of insects from said first interior chamber to said second interior chamber and for inhibiting movement of insects from said second interior chamber to said first interior chamber, and;

detector means positioned proximate a lower terminus of said second interior chamber for detecting vibration.

According to a process of the present invention, the aforementioned insect pitfall probe trap is oriented substantially vertically within an agricultural commodity and it is determined if said detector means detects vibration.

DESCRIPTION OF THE PREFERRED EMBODIMENTS

Various embodiments of the present invention are illustrated in FIGS. 1 to 5, all of which show an insect pitfall probe trap generally designated 1 which includes an insect permeable trap portion (IPTP) 3 and a reservoir portion 5. The IPTP 3 includes a first wall portion 7 defining therein a first interior chamber 11, and also defining at least one aperture 9 dimensioned to permit ingress of an insect(s) through the at least one aperture 9 and into said first interior chamber 11. The first wall portion may be of any suitable, reasonably strong and durable material including for example various metals such as brass or steel, or any of the plastic acrylics or polycarbonates such as Lexan, Plexiglas, etc., or thermosetting plastic composites used for injection molding. Preferably the first wall portion defines an array of from about 20 to about 100 apertures. While the size and shape of the apertures is selected to permit ingress of the insect(s) of interest, preferred circular aperture diameters range from about 0.11 inch (2.8 mm) to about 0.150 inch (3.8 mm). Exemplary IPTP lengths range from about 6 inches (15 cm) to about 8.5 inches (22 cm). Conveniently, a rope 13 may be affixed to the IPTP to permit the trap 1 to be held or moved by the rope. The reservoir portion 5 includes container means 15: for containing at least one insect; defining a container means interior surface 17, and; defining therein a second interior chamber 19 dimensioned to contain therein at least one insect. The present invention may employ any convenient first wall portion and reservoir portion configurations (which provide the aforementioned functions) as for example: cylindrical, or of polygonal cross-section.

As illustrated in FIGS. 1-5 the trap is provided with means positioned between said first interior chamber 11 and said second interior chamber 19 for permitting movement of insects from said first interior chamber 11 to said second interior chamber 19 and for inhibiting movement of insects from the second interior chamber 19 to said first interior chamber 11. As shown in FIGS. 1-4 such means may take the form of a frusto-conically shaped wall 27 at the lower most end of the IPTP, through which insects may easily fall from chamber 11 to chamber 19, but which inhibits insects from moving in the opposite direction. In the embodiment shown in FIG. 5 said means may take the form of a divider element 29 including: an annular portion 31 which frictionally engages the container means interior surface, and; a frusto-conical wall 33. By virtue of only frictionally engaging the interior surface, the divider element may be slid within the first wall portion and container means, and thereby permit adjustment of the relative volumes of the first and second chambers.

Figure 1:
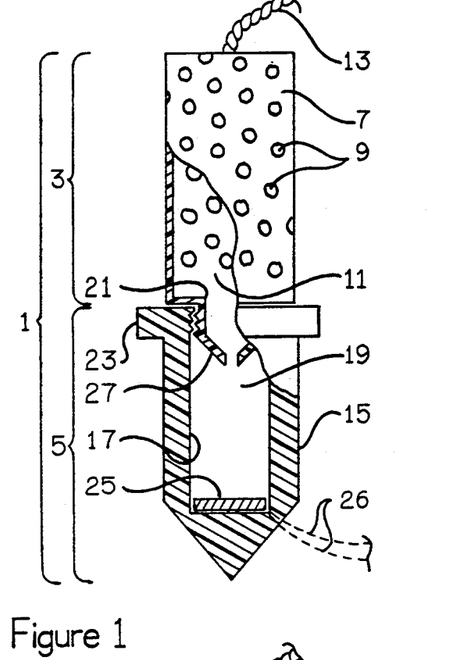
FIG. 1 is a side view of an insect pitfall probe trap of the present invention (shown partially cut away) including a reservoir portion of non-stick material.
Figure 2:
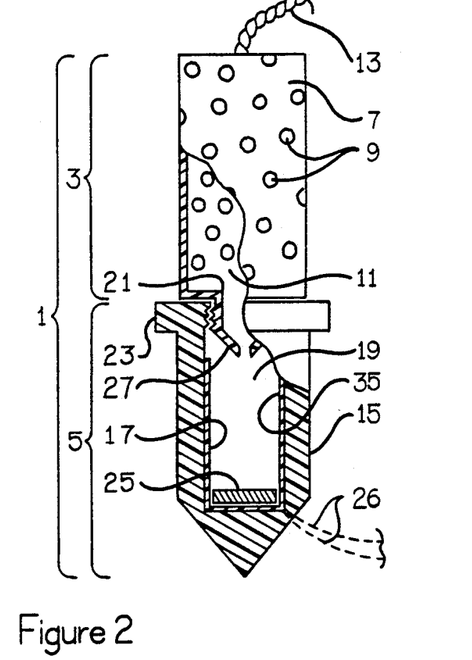
FIG. 2 is a side view of an insect pitfall probe trap of the instant invention (shown partially cut away) including a reservoir portion having a film of a non-stick material on an interior surface thereof.
Figure 3:
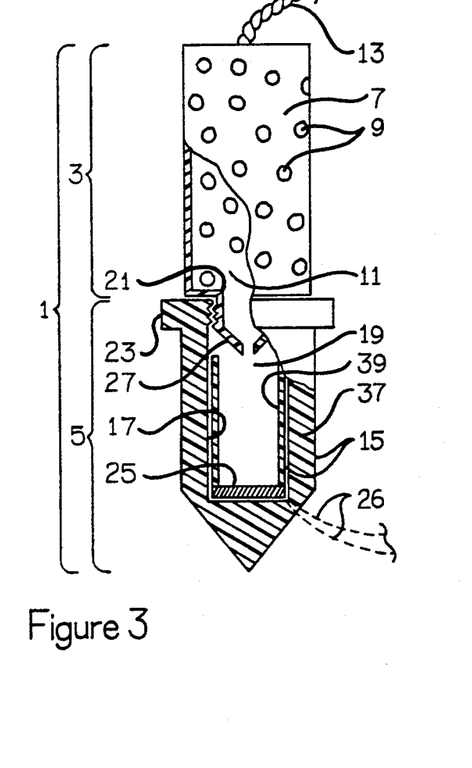
FIG. 3 is a side view of an insect pitfall probe trap of the instant invention (shown partially cut away) including an inner container means consisting essentially of non-stick material.
Figure 4:
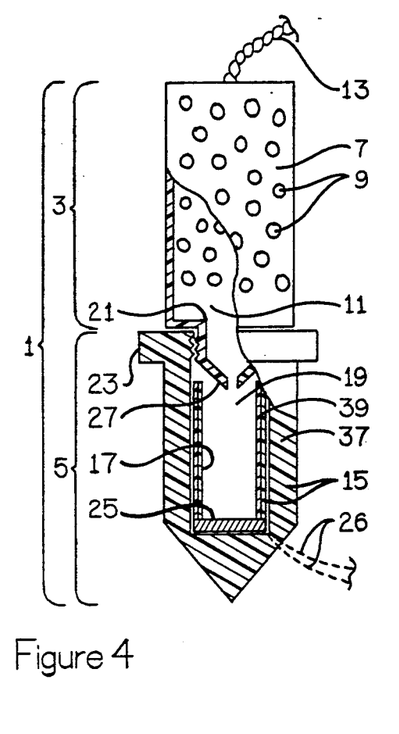
FIG. 4 is a side view of an insect pitfall probe trap of the present invention (shown partially cut away) including a film of non-stick material on an inner surface of an inner container means.
Figure 5:
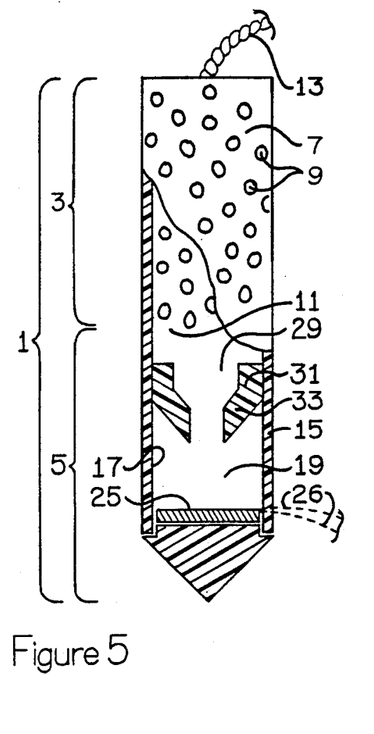
FIG. 5 is a side view of an insect pitfall probe trap of the present invention (shown partially cut away) wherein the insect permeable trap portion and reservoir portion are integral.

As shown in FIGS. 1 to 5 the IPTP is connected to the reservoir portion in such a manner that the first interior chamber is in insect-tight communication with the second interior chamber, so that an insect may move from the first interior chamber to the second interior chamber. In FIGS. 1-4 this connection is provided by a releasable connection between the IPTP and the reservoir portion i.e. a portion of the IPTP is an exteriorly threaded male connector 21 which is held within an interiorly threaded female connector (designated 23) which is part of the reservoir portion 5. An insect pitfall probe trap having the general overall configuration shown in FIGS. 1-4 (with the exception of the non-stick material and the detector means) including the aforementioned releasable connection employing threaded components, is commercially available from Agribiotech International Inc. of Winnipeg, Manitoba, Canada. It should be understood that any other convenient releasable connection may be utilized in the present invention (e.g. a bayonet type connection, cam-locking, snap ring, quick release connectors, etc.). In the embodiment illustrated in FIG. 5, the aforementioned insect-tight communication is provided by the IPTP and reservoir portion being integral with each other (e.g. a single cylinder). Clearly, this integral IPTP-reservoir structure could be utilized with the arrangements of non-stick material and detection means as shown in FIGS. 2-4 (i.e. the integral structure could be of another composition (e.g. metal, plastic) which is coated with non-stick material, or have inner container means of non-stick material or inner container means coated with non-stick material, inserted therein). An insect pitfall probe trap generally of the overall configuration shown in FIG. 5 (with the exception of the non-stick material and detection means) is commercially available from Grain Guard, Inc. of Verona, Wis.

In accordance with the present invention, and as illustrated in each of FIGS. 1-5, detector means for detecting vibration (designated 25) is positioned proximate the lower terminus of the second interior chamber 19. The detector means 25 may for example be a microphone, a piezoelectric disc or a piezoelectric sheet, i.e. and thus function to provide an electrical signal indicative of vibration detection. Examples of such detector means useable in the present invention include Kynar piezo film or a MU-RATA (Smyrna, Ga.) Model PKM11-A-40 piezo disc. Means, such as wires 26, may be utilized for providing electrical communication between the detector means and the exterior of the trap. Two wires are shown for purposes of illustration only.

The container means 15 includes on at least the interior surface thereof 17, a non-stick material upon which insects cannot readily climb. An example of such non-stick material is TEFLON TM (i.e. polytetrafluoroethylene and fluorinated ethylene-propylene resins). The purpose of the non-stick material is to substantially prevent the insect(s) within chamber 19 from crawling off of the detector means 25. For ease of manufacture the entire container means 15 may consist essentially (or consist solely) of such non-stick material, as in the embodiments shown in FIGS. 1 and 5. In these embodiments, the detector means is positioned within the second interior chamber proximate the bottom thereof. Alternatively, as shown in FIG. 2 the non-stick material may be a film 35 on the container means interior surface 17. This provides the advantage over the embodiment of FIG. 1 of requiring less non-stick material.

In the embodiment illustrated in FIG. 3, the container means 15 includes an outer container means 37 and an inner container means 39 within said outer container means. In this embodiment the inner container means 39 defines the second interior chamber 19 and the inner container means consists essentially (or consists solely) of non-stick material e.g. the inner container may be a discrete length of non-stick (e.g. TEFLON TM) tubing, which would not require application of a non-stick film. As illustrated in FIG. 3 the inner container means 39 may be a cylinder open at both ends with a disc shaped detector means (of a diameter approximately equal to the outside diameter of the inner container means) positioned (e.g. affixed, as for example by gluing) proximate the lower terminus of the inner container means e.g. covering the lowermost open end of the cylinder. This embodiment has the advantages of: (1) ease of manufacture (i.e. no need to apply a film), and; (2) that it permits retrofitting of a trap i.e. by simply opening the trap (separating the IPTP and reservoir portion) inserting the inner container means 39 and detector means 25 therein and extending the wire(s) out of the trap.

The embodiment of FIG. 4 is similar to that of FIG. 3 in many respects (e.g. the container means includes an outer container means 37 and an inner container means 39 within said outer container means) however, in order that less non-stick material may be used, the non-stick material is provided as a film on the inner surface of the inner container means (i.e. the container means interior surface 17 is the inner surface of the inner container means 39). Thus, in this embodiment the inner container means may for example be made of: glass, brass, plastic, etc.; with a film of the aforementioned non-stick material on the inner surface thereof. In this embodiment as well as the previous embodiment, the inner container means may: (1) be of sufficient diameter to fit snugly into the outer container means 37, and; (2) be of sufficient length to extend from the bottom of the second interior chamber 19 to the proximity of the wall 27 or in direct contact with the wall 27. For example the inner container means may conveniently be a cylinder of 20 millimeters outer diameter and 63 millimeters length, but the size may be varied to accomodate a variety of pitfall traps without changing the performance of the device.

In use, a pitfall trap(s) of the present invention, may be placed in an agricultural commodity container (e.g. truck, ship (e.g. boat, barge, etc.), railroad car, storage bin (e.g. silo, grain elevator), etc.) either before the container is filled or after filling by use of extension insertion pipes. Placing the traps before filling, especially in tall silos, allows the traps to be placed at all storage levels. Insects which enter the insect permable trap portion fall through the aperture in the frusto-conical wall into the second interior chamber 19. Because of the non-stick material the captured insects are confined to the detector means 25. The movements (e.g. walking, falling, etc.) of these confined insects set up vibrations which are detected by the detector means. Captured insects in the trap typically live for only a week or less, dying from starvation. Since dead insects which may have accumulated from the beginning of the storage period do not cause the detection means to produce electrical impulses, the output from the detection means gives an indication of the number of insects captured in the proceding week. Thus, the output of the detection means at any time during the storage period is an indication of the insect infestation level of the grain at that time.

Figure 7:
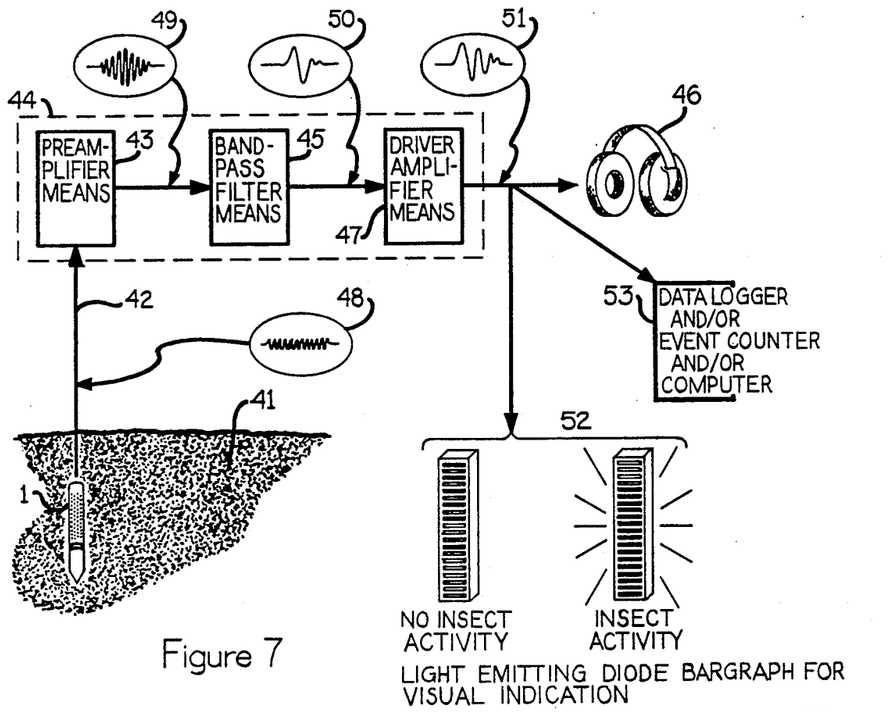
FIG. 7 is a schematic representation of a system of the present invention, illustrating the relationship of the basic components.

FIG. 7 is a simplified block diagram of basic electronic components which may be utilized in the present invention. As shown in FIG. 7 the insect pitfall probe trap 1 is positioned substantially vertically within an agricultural commodity 41. Vibrations produced by insects in the insect pitfall probe trap 1 produce relatively low-level electronic signals 48 which are transmitted through a shielded cable 42 to an electronic filter and amplifier designated 44. These low level signals are electrically transmitted through shielded cable 42 to the preamplifier means 43 (e.g. a Radio Shack model number 277-10088) which is the input stage for the combination amplifier-filter 44 (the components of which are shown in FIG. 7 in a dashed rectangle). A bandpass filter means 45 may be provided. Bandpass filtering may be as simple as a 0.01 microfarad coupling capacitor which takes the preamplified signal 49 and filters out those frequencies above and below the desired frequencies. The filtered signal 50 then goes to the input of the driver amplifier means 47 (which may for example be a model 32-2031A from Radio Shack) which amplifies this preconditioned signal to a signal of sufficient level 51 to drive a pair of headphones 46, or other audio or visual indicator means such as a gauge, meter, dial or display (e.g. a 20-segment red-light-emitting diode array available from National Semiconductor, Santa Clara, Calif.) (designated 52), incorporated in the device using two IM-3914 integrated circuits available from Radio Shack, Mouser, Digi-key or other electronic suppliers). Use of such a display(s) when used in combination with the headphones gives a visual reinforcement to the audio signals produced by insect activity. Also, the device of FIG. 7 may include a radio transmitter used in addition to or in place of the headphones or other indicator means. The embodiment illustrated in FIG. 7 may also employ a data logger (for recording detection of vibration) and/or event counter and/or computer designated 53 (such as a B&K Precision frequency counter model number 1803). A combination portable, battery operated amplifier and frequency counter would be very convenient and could be easily constructed with existing technology. Computer equipment is currently in place at most large grain elevators to monitor grain temperature and moisture. Thus the present invention may easily be implemented by integration into such existing monitoring systems, and utilizing the same computer to both provide the aforementioned monitoring and collect insect infestation data from the grain probe trap(s). Since the number of voltage spikes emanating from the detector means is proportional to the number of captured insects, the greater the number of voltage spikes the greater the number of captured insects. Thus, a calibration may be made, to permit estimation of the number of captured insects based on the number of voltage spikes.

Figure 8:
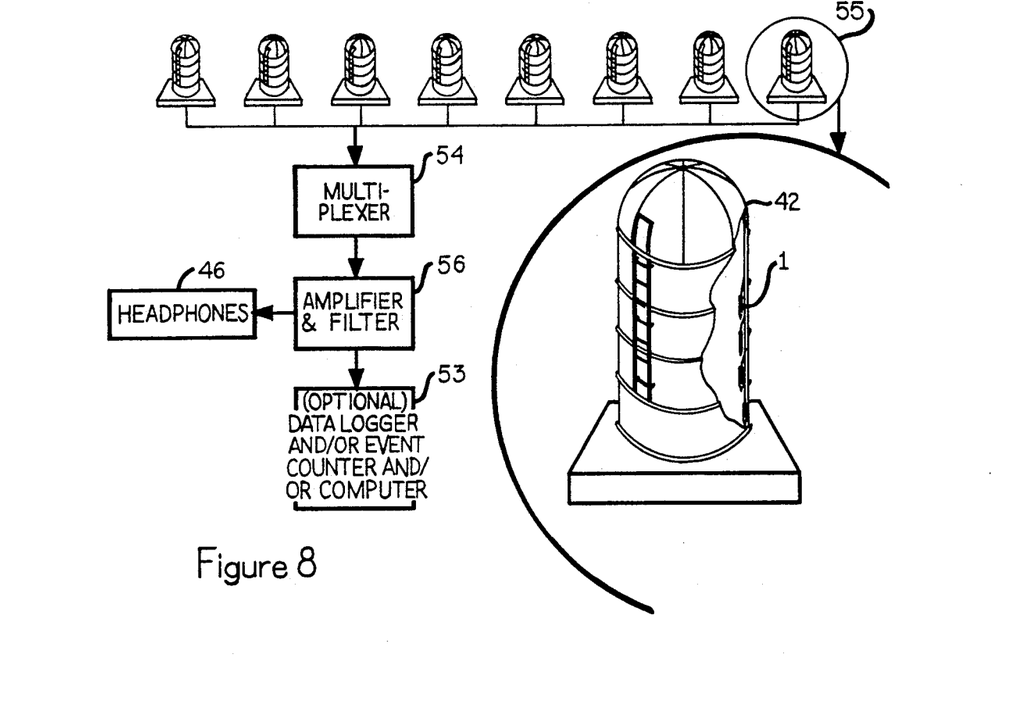
FIG. 8 is a schematic representation illustrating a manner in which insect pitfall probe traps may be utilized to monitor and detect insects in a multi-container (e.g. silo) storage complex.

FIG. 8 illustrates how the insect pitfall probe traps of the present invention may be used to monitor and detect insects in a multi-container (e.g. multi-silo) storage complex. As illustrated in the inset in FIG. 8, one or more of the probe traps 1 may be placed within each of one or more agricultural commodity containing silos designated 55. While eight such silos are shown for purposes of illustration, it should be understood that any number of such silos may be utilized in the present invention. Each probe is connected, either by direct electronic connection (e.g. wires) or via a radio transmitter to a multiplexer 54. When wires are used, the wires from the detector means along with the trap ropes lead to the surface of the agricultural commodity at the top of the container. The multiplexer 54 conveys the electronic signals indicative of the input to an amplifier and filter 56. Subsequently, the signal is transmitted to an indicator means such as headphones 46, and an optional data logger and/or event counter and/or computer 53. Thus the present invention encompasses using a plurality of traps, and means in electronic communication with the detector means of each of the traps, for receiving electronic signals from the traps indicative of detection of vibration. The computer or other analogous device may be utilized to monitor the grain probes in the storage complex and periodically print out or display the insect infestation status for the entire storage complex. The computer outputs data for each trap to alert the warehouseman about insect problems anywhere in the silos. This information would then be used to decide which agricultural commodity would need to be used first, which could be safely stored for a longer time, which agricultural commodity would need to be fumigated, etc. One of the tremendous advantages of this embodiment is that after the initial installation of the probe traps there is virtually no labor involved. Alternatively, the wires from the detector means may be brought out to a bulkhead above the grain. Warehousemen, inspectors, etc. could attach a portable amplifier and frequency counter to the wires to collect data on the numbers of insects in the traps below. Thus, the most expensive parts of the equipment (amplifier and frequency counter) could be used for several warehouses, cutting down on instrument costs. A third alternative would have the warehouseman, inspector, etc. connect the wires from a detector means to a portable amplifier, the output of which would lead to earphones. The inspector could tell whether the trap had captured insects and thus whether there was any need to pull the trap from the agricultural commodity. This would save a lot of inspection time by avoiding the pulling of empty traps from the agricultural commodity and would allow the inspector to leave deep traps in the agricultural commodity until they contained insects.

Figure 9:
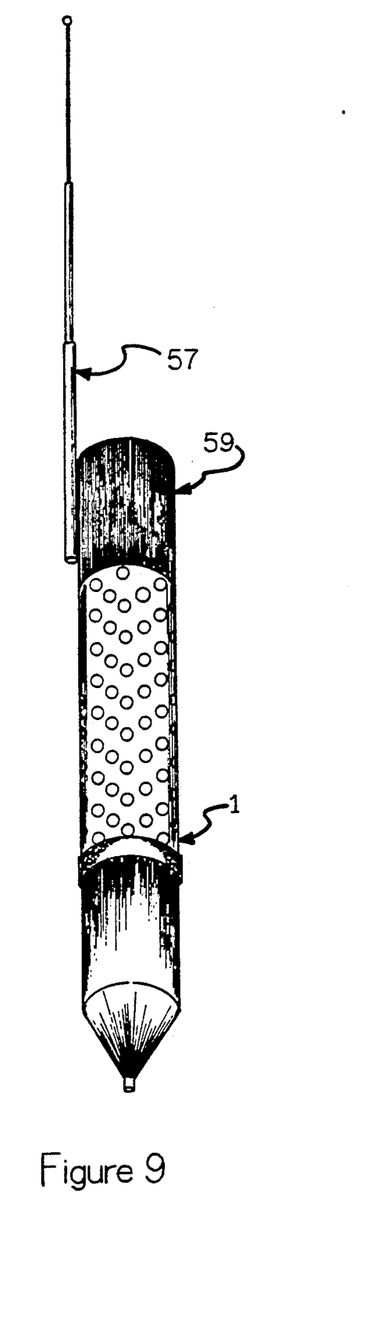
FIG. 9 is a side view of an insect pitfall probe trap of the instant invention, with a radio transmitter, which permits remote insect monitoring.
Figure 10:
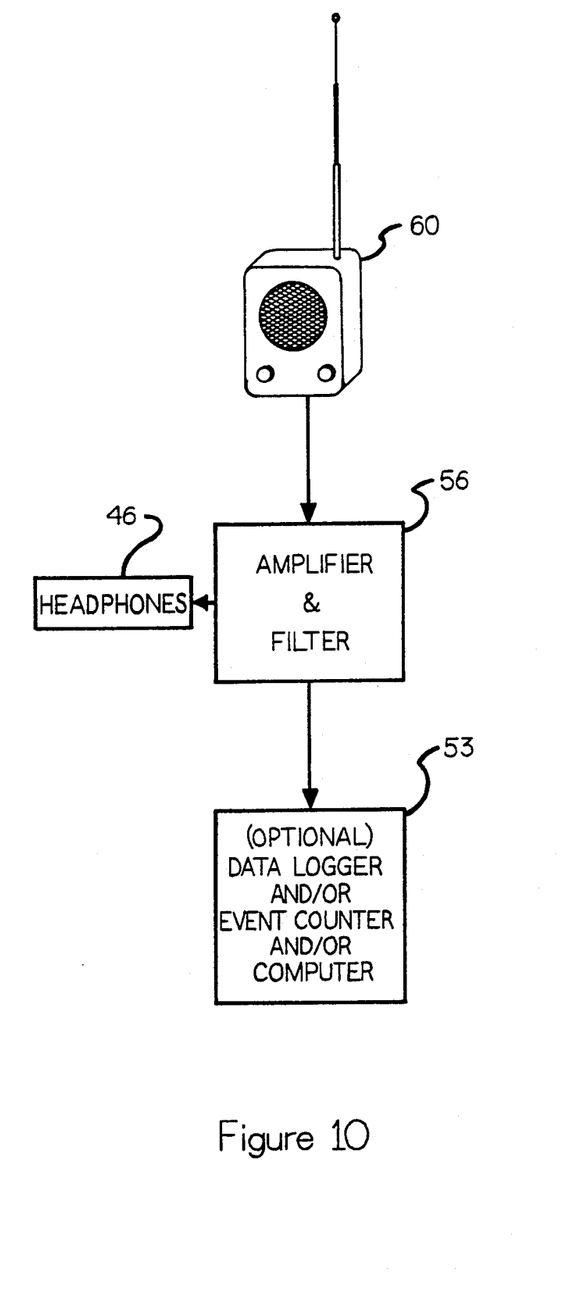
FIG. 10 is a schematic illustration of a radio receiver for use in receiving radio signals from insect pitfall probe traps.

The probe trap shown in the embodiment of FIG. 9 is adapted for communication via an amplifier equipped with a radio transmitter 59 (e.g. an amplifier equipped with a FM transmitter, such as a model WM002T from RCA) and a transmitter antenna 57, and thereby permits remote wireless insect monitoring. The radio transmitter functions to transmit a radio signal indicative of detection of vibration by said means for detecting vibration to a radio receiver means. FIG. 10 illustrates a system which may be utilized to receive radio transmissions from a device such as that of FIG. 9. This system includes a radio (e.g. FM) receiver means and speaker 60, which directs a signal to an amplifier and filter 56. The amplified and filtered signal is directed to an indicator means (including one or more of the aforementioned indicator means) such as headphones 46, and optionally to a data logger and/or event counter and/or computer 53. Use of such a transmitter and receiver: allows convenient remote monitoring; permits the signals from a plurality of such detection devices to be monitored at a single location, and facilitates making permanent records of insect activity, especially when the detection device(s) is/are in a location (such as on top of a tall grain elevator or silo) where transporting and/or operating recording devices such as magnetic tape recorders or paper tape strip chart recorders would be awkward or hazardous.

Any of the aforementioned devices of the present invention may employ a variety of power sources including, battery and/or A.C. power. When battery power is utilized it may be desirable to utilize conventional means for indicating low battery voltage, such as the commercially available ICM 7201 Low Battery Voltage Indicator available from Intersil, Capertino, Calif. This device lights a red warning light when the battery voltage is low; i.e. the battery needs replacement or recharging.

The present invention may be utilized to detect infestation by a variety of different insects such as: red flour beetle, *Triholium castaneum* (Herbst); lesser grain borer, *Rhyzopertha dominica* (F.); rice weevil, *Sitophilus oryzae* (L.); rusty grain beetle, *Cryptolestes ferrugineus* (Stephens); saw tooth grain beetle, *Oryzaephilus surinamensis* (L.); in numerous types of agricultural commodities including corn, wheat, rice, seeds, nuts, oats, barely, cotton and any similar agricultural commodity which may be infested during storage.

The following example is intended only to further illustrate the invention, and is not intended to limit the scope of the invention which is defined by the claims.

EXAMPLE

The inner container means consisted of a piezoelectric disc detector means (model PKM11-A40, MURATA Company, Smyrna, Ga.) glued to a 63 mm-long×20 mm-O.D. (14 mm I.D.) TEFLON TM coated glass cylinder. The piezoelectric disc formed the bottom of the cylinder and the top of the cylinder was left open. This inner container means was placed in the reservoir portion of the insect pitfall probe trap (manufactured by Agribiotech International Inc., Winnipeg, Manitoba, Canada) with the open end toward the insect permeable portion such that insects which entered the insect permeable trap portion would fall onto the piezoelectric disc which formed the floor of the inner container means located in the reservoir portion of the insect pitfall probe trap. Vibrations set up by the movement of captured insects on the detector means create voltage spikes which are counted by a computer controlled data collection system consisting of a model 3700 Krohn-Hite bandpass filter with 20 dB gain (bandpass filter set at 0.5 to 20 KHz). A model 2610 Bruel and Kjear amplifier, model 5316A Hewlett Packard universal counter and a model 87 Hewlett Packard computer complete the system. Amplified voltage spikes that exceeded a threshold of 0.05 volts were counted.

Various numbers (between 1 and 20) of 1 to 14 day old lesser grain borers, *Rhyzopertha dominica* (F.), were inserted through the apertures of the insect permeable trap portion and allowed to drop into the inner container means. The number of voltage spikes produced as result of insect activity per 1 minute interval was determined for each batch of insects. Tests were replicated 10 times.

Figure 6:
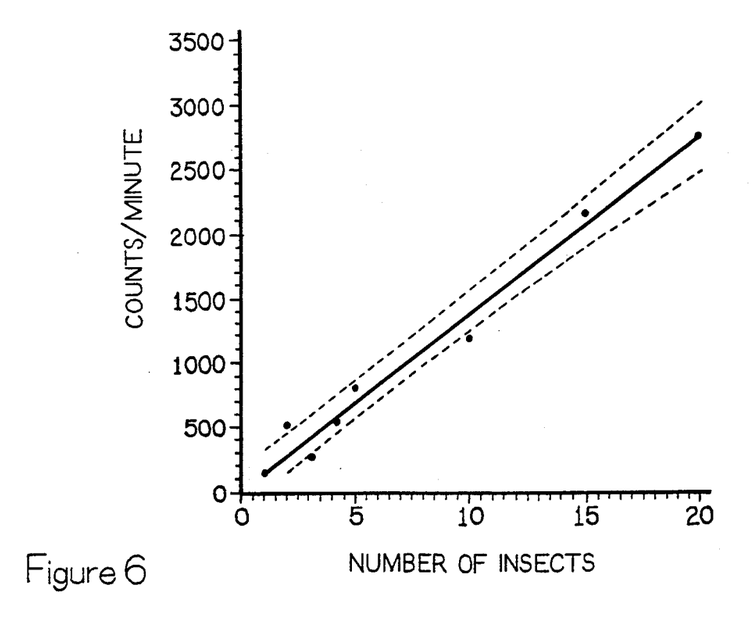
FIG. 6 is a graph of counts per minute versus number of insects as measured with a device of the present invention described in the following example.

FIG. 6 is a calibration curve relating the number of voltage spikes (counts) detected by the event counter per minute to the number of lesser grain borers in the inner container means. Each data point is the average of 10 replicates. The solid line is the regression line computed by a standard regression statistical analysis and the dashed lines are the 95% confidence intervals computed by a standard statistical analysis. This calibration curve could be used to relate voltage spikes (counts) displayed from an event counter for a particular trap to the number of insects captured in that trap.

The foregoing detailed description and example are given merely for purposes of illustration. Modification and variations may be made therein without departing from the spirit and scope of the invention.

INDEX OF APPARATUS ELEMENTS 1. insect pitfall probe trap
3. insect permeable trap portion (IPTP)
5. reservoir portion
7. first wall portion
9. aperture(s)
11. first interior chamber
13. rope
15. container means
17. container means interior surface
19. second interior chamber
21. male connector
23. female connector
25. detector means
26. wires
27. frusto-conical wall
29. divider element
31. annular portion
33. frusto-conical wall
35. non-stick film
37. outer container means
39. inner container means
41. agricultural commodity
42. shielded cable
43. preamplifier means
44. electronic filter and amplifier
45. bandpass filter means
46. headphones
47. driver amplifier means
48. low-level electrical signals
49. preamplified signal
50. filtered signal
51. amplified signal
52. light emitting diode bargraph
53. data logger and/or event counter and/or computer
54. multiplexer
55. agricultural commodity containing silo
56. amplifier and filter
57. transmitter antenna
59. amplifier equipped with a radio transmitter
60. radio receiver means and speaker

We claim:

1. A process for detecting insect infestation in an agricultural commodity comprising:
   providing an insect pitfall probe trap including:
   an insect-permeable trap portion including a first wall portion defining therein a first interior chamber, said first wall portion defining at least one aperture dimensioned to permit ingress of an insect through said at least one aperture into said first interior chamber, a reservoir portion including container means for containing at least one insect and defining a container means interior surface, said container means defining therein a second interior chamber dimensioned to contain therein at least one insect, said container means including on at least said interior surface thereof a non-stick material upon which insects cannot readily climb, said insect-permeable trap portion being connected to said reservoir portion whereby said first interior chamber is in insect-tight communication with said second interior chamber so that an insect may move from said first interior chamber to said second interior chamber, means positioned between said first interior chamber and said second interior chamber for permitting movement of insects from said first interior chamber to said second interior chamber and for inhibiting movement of insects from said second interior chamber to said first interior chamber, and detector means positioned proximate a lower terminus of said second interior chamber for detecting vibration;

orienting said insect pitfall probe trap substantially vertically within an agricultural commodity, and;

determining if said detector means detects vibration.

2. The process of claim 1 further including providing a plurality of said insect pitfall probe traps, and means in electronic communication with the detector means of each of said plurality of traps for receiving electronic signals from said traps indicative of detection of vibration.

3. The process of claim 1 wherein said insect-permeable trap portion and said reservoir portion are integral.

4. The process of claim 1 wherein said insect-permeable trap portion and said reservoir are connected by a releasable connection.

5. The process of claim 4 wherein said releasable connection is provided by connectors selected from the group consisting of: male and female threaded components, bayonet, cam-locking or snap ring quick-release connectors.

6. The process of claim 1 wherein said detector means is selected from the group consisting of a microphone, a piezoelectric disc and a piezoelectric sheet.

7. The process of claim 1 wherein said detector means provides an electrical signal indicative of vibration detection, and further including the steps of filtering and amplifying said electrical signal.

8. The process of claim 1 further including a step of telemetering including transmitting a radio signal indicative of detection of vibration by said means for detecting vibration to a radio receiver means.

9. The process of claim 1 wherein said step of determining includes indicating said vibration detecting with an audio or visual indicator means.

10. The process of claim 1 further including the step of recording detection of vibration.

11. The process of claim 1 wherein said non-stick material is a film on said container means interior surface.

12. The process of claim 1 wherein said container means consists essentially of said non-stick material.

13. The process of claim 1 wherein said container means includes: an outer container means, an inner container means within said outer container means, said inner container means defining therein said second interior chamber, and said container means interior surface being an inner surface of said inner container means;

wherein said detector means is positioned proximate a lower terminus of said inner container means and, wherein said non-stick material is a film on said inner surface of said inner container means.

14. The process of claim 1 wherein said container means includes: an outer container means, an inner container means within said outer container means, said inner container means defining therein said second interior chamber, and said inner container means consisting essentially of said non-stick material and, wherein said detector means is positioned proximate a lower terminus of said inner container means.

15. An apparatus for detecting insect infestation in an agricultural commodity comprising:

an insect-permeable trap portion including a first wall portion defining therein a first interior chamber, said first wall portion defining at least one aperture dimensioned to permit ingress of an insect through said at least one aperture into said first interior chamber;

a reservoir portion including container means for containing at least one insect and defining a container means interior surface, said container means defining therein a second interior chamber dimensioned to contain therein at least one insect, said container means including on at least said interior surface thereof a non-stick material upon which insects cannot readily climb;

said insect-permeable trap portion being connected to said reservoir portion whereby said first interior chamber is in insect-tight communication with said second interior chamber so that an insect may move from said first interior chamber to said second interior chamber;

means positioned between said first interior chamber and said second interior chamber for permitting movement of insects from said first interior chamber to said second interior chamber and for inhibiting movement of insects from said second interior chamber to said first interior chamber, and;

detector means positioned proximate a lower terminus of said second interior chamber for detecting vibration.

16. The apparatus of claim 15 further including means in electrical communication with said detector means for determining if said detector means detects vibration.

17. The apparatus of claim 15 wherein said insect-permeable trap portion and said reservoir portion are integral.

18. The apparatus of claim 15 wherein said insect-permeable trap portion and said reservoir portion are connected by a releasable connection.

19. The apparatus of claim 18 wherein said releasable connection is provided by connectors selected from the group consisting of: male and female threaded components, bayonet, cam-locking, or snap ring quick-release connectors.

20. The apparatus of claim 15 wherein said detector means is selected from the group consisting of a microphone, a piezoelectric disc and a piezoelectric sheet.

21. The apparatus of claim 15 wherein said detector means provides an electrical signal indicative of vibration detection, and further including means, in electrical communication with said detector means, for filtering and amplifying said electrical signal.

22. The apparatus of claim 15 further including radio transmitter means, in electrical communication with said detector means, for transmitting a radio signal indicative of vibration detection by said detector means.

23. The apparatus of claim 22 further including radio receiver means for receiving said radio signal transmitted by said radio transmitter means.

24. The apparatus of claim 15 further including audio or visual indicator means, in electrical communication with said detector means, for indicating said vibration detection by said detector means.

25. The apparatus of claim 15 further including recording means, in electrical communication with said detector means, for recording said vibration detection by said detector means.

26. The apparatus of claim 15 wherein said non-stick material is a film on said container means interior surface.

27. The apparatus of claim 15 wherein said container means consists essentially of said non-stick material.

28. The apparatus of claim 15 wherein said container means includes: an outer container means, an inner container means within said outer container means, said inner container means defining therein said second interior chamber, and said container means interior surface being an inner surface of said inner container means;

wherein said detector means is positioned proximate a lower terminus of said inner container means and, wherein said non-stick material is a film on said inner surface of said inner container means.

29. The apparatus of claim 15 wherein said container means includes: an outer container means, an inner container means within said outer container means, said inner container means defining therein said second interior chamber, and said inner container means consisting essentially of said non-stick material and,     wherein said detector means is positioned proximate a lower terminus of said inner container means.

* * * * *